(12) United States Patent
Ulbrich et al.

(10) Patent No.: US 7,919,076 B2
(45) Date of Patent: Apr. 5, 2011

(54) PH-SENSITIVE POLYMERIC CONJUGATES OF AN ANTHRACYCLINE CANCEROSTATIC DRUG FOR TARGETED THERAPY

(75) Inventors: Karel Ulbrich, Prague (CZ); Tomas Etrych, Prague (CZ); Blanka Rihova, Prague (CZ); Marketa Jelinkova, Prague (CZ); Marek Kovar, Prague (CZ)

(73) Assignee: Zentiva, k.s. (CZ)

( * ) Notice: Subject to any disclaimer, the term of this patent is extended or adjusted under 35 U.S.C. 154(b) by 1554 days.

(21) Appl. No.: 10/499,422

(22) PCT Filed: Dec. 20, 2002

(86) PCT No.: PCT/CZ02/00070
§ 371 (c)(1), (2), (4) Date: Oct. 3, 2005

(87) PCT Pub. No.: WO03/053473
PCT Pub. Date: Jul. 3, 2003

(65) Prior Publication Data
US 2006/0057099 A1    Mar. 16, 2006

(30) Foreign Application Priority Data
Dec. 20, 2001    (CZ) ..................................... 4653-01

(51) Int. Cl.
*A61K 31/74*    (2006.01)
(52) U.S. Cl. ................................................... 424/78.17
(58) Field of Classification Search ........................ None
See application file for complete search history.

(56) References Cited

U.S. PATENT DOCUMENTS
5,037,883 A    8/1991    Kopecek et al. ............. 525/54.1

OTHER PUBLICATIONS

Mukaiyama, Tetrahedron, 1999, 55, 8609-8670.*
Choi et al., Journal of Bioactive and Compatible Polymers (1999) 14(6):447-456.
Etrych et al., J. Controlled Rel. (2001) 73(1):89-102.
International Search Report for PCT/CZ02/00070, mailed on Jul. 31, 2003, 3 pages.
Julyan et al., J. Control. Rel. (1999) 57:281-290.
Kopeček et al., Europ. J. Pharm. Biopharm. (2000) 50:61-81.
Kratz et al., Critical Reviews "in Therapeutic Drug Carriers Systems" (1999) 16(3):245-288.
Lu et al., Bioconjugate Chemistry (2001) 12(1):129-133.
Říhová et al., J. Controlled Release (2001) 74(1-3):225-232.
Solovskij et al., Biomaterials (1983) 4(1):44-48.
Thomson et al., Br. J. Cancer (1999) 81:99-107.
Ulbrich et al., J. Controlled Rel. (2000) 64:63-79.
Ulbrich et al., J. Controlled Rel. (2003) 87(1-3):33-47.
Vasey et al., Clinical Cancer Research (1999) 5:83-94.

\* cited by examiner

*Primary Examiner* — Michael G Hartley
*Assistant Examiner* — Paul Dickinson
(74) *Attorney, Agent, or Firm* — Morrison & Foerster LLP (57) ABSTRACT

Conjugates consisting of a polymeric carrier constituted by 30 to 3,000 monomer units linked to form a polymeric chain, composed of a) 60 to 99% of N-(2-hydroxypropyl)methacrylamide units, b) 1 to 25% of units of methacryloylated hydrazones of α-amino acids, ε-amino acids, aromatic amino acids or oligopeptides terminated with a molecule of an anthracycline cancerostatic, c) 0.5 to 15% of units of methacryloylated α-amino acids, ε-amino acids, aromatic amino acids or oligopeptides or their sodium salts.

20 Claims, 8 Drawing Sheets

FIG. 1: The structure of a non-targeted polymeric drug. A conjugate having x = 94 % mol., a = 3 % mol., b = 2 % mol., c = 1 % mol. and X = AB or AKap when using an amino acid and GlyPheLeuGly when using an oligopeptide was beneficially used for biological experiments.

Fig. 2 Scheme of preparation and structure of branched high-molecular conjugates. The suitable molecular weight of the conjugate is 120,000 g/mol. The content of crosslinks, DOX, hydrazone groups and carboxyls is 0.5 % mol., 9 % wt., 2 %mol. and 2 %mol, respectively.

Fig. 3: A general structure of a targeted polymeric drug. A conjugate having x = 92 % mol., a = 3 % mol., b = 0.7 % mol., c = 2 % mol., d = 2.3 % mol. and X = AB or AKap when using an amino acid as a spacer and GlyPheLeuGly when using an oligopeptide was beneficially used for biological experiments.

X = α-amino acid, ε-amino acid, aromatic amino acid, or oligopeptide

S, for a macromolecular polymer, is a biodegradable oligopeptide link containing the GlyPheLeuGly, GlyPheGly or similar sequence, and binding other polymeric chains FIG. 4: Structure of polymeric precursors.

Fig. 5 Results of measuring the release rates of doxorubicin from polymers differing in the spacer composition; A) at a pH modeling the endosome environment (pH 5); B) at a pH modeling the blood pH (7.4). The drug content in the conjugates was 10 % wt.

Fig. 6 Comparison of *in vitro* inhibition activities of samples containing drugs bound by various links; tested line of murine leukemia EL4 (T-cellular lymphoma EL4).

| Sample | $IC_{50}$ (µg DOX/ml) |
|---|---|
| P-GFLG-DOX (PK1) | 19.1* |
| P-GG-DOX (hydrazone) | 0.40 |
| P-GFLG-DOX (hydrazone) | 0.26 |
| P-p-amino benzoic-DOX (hydrazone) | 0.04 |
| P-ε-amino caproic-DOX (hydrazone) | 0.08 |
| Doxorubicin (DOX) | 0.02 |

$IC_{50}$ is the drug concentration causing 50 % inhibition of proliferation.

Fig. 7 Comparison of *in vitro* inhibition activities of samples containing drugs bound by various links; tested erythroleukemic line K 562.

| Sample | IC$_{50}$ (µg DOX/ml) |
|---|---|
| P-GFLG-DOX (PK1) | 9.71* |
| P-GG-DOX (hydrazone) | 0.06 |
| Doxorubicin (DOX) | 0.28 |

IC$_{50}$ is the drug concentration causing 50 % inhibition of proliferation.

Fig. 8 *In vivo* anti-tumor activity of polymeric conjugates containing hydrolytically released doxorubicin (protective regimen); T-cellular lymphoma EL4: $10^5$ of cells/ mouse, s.c.

PH-SENSITIVE POLYMERIC CONJUGATES OF AN ANTHRACYCLINE CANCEROSTATIC DRUG FOR TARGETED THERAPY

CROSS-REFERENCE TO RELATED APPLICATION

This application is the national phase of PCT application PCT/CZ02/00070 having an international filing, date of 20 Dec. 2002, which claims priority from Czech Republic application No. PV 2001-4653 filed 20 Dec. 2001. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 321402000500Seqlist.txt | Dec. 14, 2010 | 795 bytes |

TECHNICAL FIELD

The invention involves polymeric anti-cancer drugs which enable targeted transport in the body and are focused on targeted tumor therapy in human medicine.

BACKGROUND ART

The development of new drugs and drug forms has been recently more and more focused on the utilization of polymeric substances, especially water-soluble polymers, as drug carriers. A number of polymeric conjugates of cancerostatic drugs and soluble polymers, in which the tumor drug was attached to the polymer by a non-cleavable covalent bond, a hydrolytically unstable ionic bond or a covalent bond susceptible to enzymatic or simple hydrolysis, have been prepared and studied. This endeavor was aimed to prepare drugs with enhanced pharmacokinetic and pharmacodynamic behavior, enabling targeted therapy of tumors. Polymeric drugs prepared on the basis of HPMA copolymers form an important group. The anti-cancer drug in such substances is attached to a polymeric N-(2-hydroxypropyl)methacrylamide carrier by an enzyme-cleavable oligopeptide sequence, prepared as a substrate for lysosome enzymes (enzymes present in mammalian cells). The structure, synthesis and properties of such conjugates have been described in a patent [Duncan 1985]. The results obtained in this area up to now have been clearly summarized by Kopeček et al [Kopeček et al 2000]. The above polymeric drugs have been effective in the treatment of a number of tumors in mice and rats. At present, two of the polymeric conjugates are even being tested clinically. [Vasey 1999 et al, Julyan et al 1999, Thomson et al 1999]. The results of such clinical testing have shown that a polymeric conjugate of doxorubicin has lower non-specific toxicity than a free drug. Its maximum allowed amount (MAA) is 320 mg/m$^2$ which is 4 to 5 times higher than the clinical amount of free doxorubicin (60-80 mg/m$^2$) normally used. No significant effect on the cardiac functions has been observed after the administration of the polymeric drug, although the individual cumulative amount reached up to 1680 mg/m$^2$. All the other areas of toxicity observed in connection with the administration of free, i.e. non-directed anthracycline antibiotics have been significantly reduced. One of the disadvantages of the polymeric conjugate drugs clinically tested is a relatively low specificity of effect since such conjugates either contain no targeting unit at all, such as PK1, or contain a carbohydrate of a relatively low specificity (galactosamine in the PK2 conjugate in which the ability to direct a polymeric drug to the liver is being tested). Therefore, conjugates in which the aimed specific effect is achieved by attaching a specific targeting molecule (e.g. antibodies, as well as lectin, the growth hormone, transferin, etc.) to the carrier molecule are being developed.

Another disadvantage of the clinically tested conjugates, including those of poly(HPMA) and doxorubicin, is the fact that the drug in its pharmacologically active form is only released from such conjugates in cells by an enzymatic reaction which occurs in lysosomes. This means that the drug is only effective in cells with a high concentration of lysosome enzymes—peptidases. Another disadvantage is a relatively complex structure of the conjugate requiring the inclusion of a sequence from which the drug is released by peptidases, mostly the GlyPheLeuGly (SEQ ID NO:1) tetrapeptide link, which makes the synthesis more expensive and complicated.

Papers provide plenty of information on the preparation and studies of properties of polymers to which a cancerostatic drug is attached by a bond susceptible to hydrolysis in an aqueous medium. The results have been summarized by Kratz [Kratz et al, 1999]. Natural macromolecules, such as albumin, dextrans, transferin, alginates or antibodies, have mostly been used as carriers for cancerostatic drugs. Synthetic polymeric carriers, poly(ethylene glycol) and polyglutamines, have been used in a few cases. The drugs were attached to the carriers by bonds enabling the hydrolysis-controlled release of the active drug both in the extracellular space and inside the cells. In case of doxorubicin (Dox), the bond was most frequently formed by esters of cis-aconityl acid or it was a hydrazone bond. However, in vivo testing of all the above pH-sensitive conjugates in animals has not provided conclusive results. Therefore, none of the polymeric conjugates has been used or clinically tested for tumor treatment.

The polymeric cancerostatic drugs developed by us and prepared on the basis of copolymers of HPMA and a cancerostatic drug linked by a pH-sensitive hydrazone bond have shown, in both in vitro and in vivo tests in mice, a significantly higher anti-tumor efficacy in relation to a number of tumor lines compared to conjugates with the drug attached to the polymeric carrier by an enzyme-cleavable bond via an oligopeptide link. The synthesis of such conjugates compared with the poly(HPMA) conjugates developed earlier is more simple, less expensive and easier to manage since one amino acid only can be used as a link instead of the enzyme-degradable oligopeptide sequence and bonding of the drug to the polymer is a simple reaction. The drug is released as a result of a change of pH in the medium and therefore the presence of lysosome enzymes is not essential for activation. The rate of such release (and therefore the immediate cytostatic concentration) is much higher compared to conjugates containing sequences only degradable by enzymes. [Ríhová et al, 2001, Etrych et al, 2001].

DISCLOSURE OF INVENTION

Figure 3:
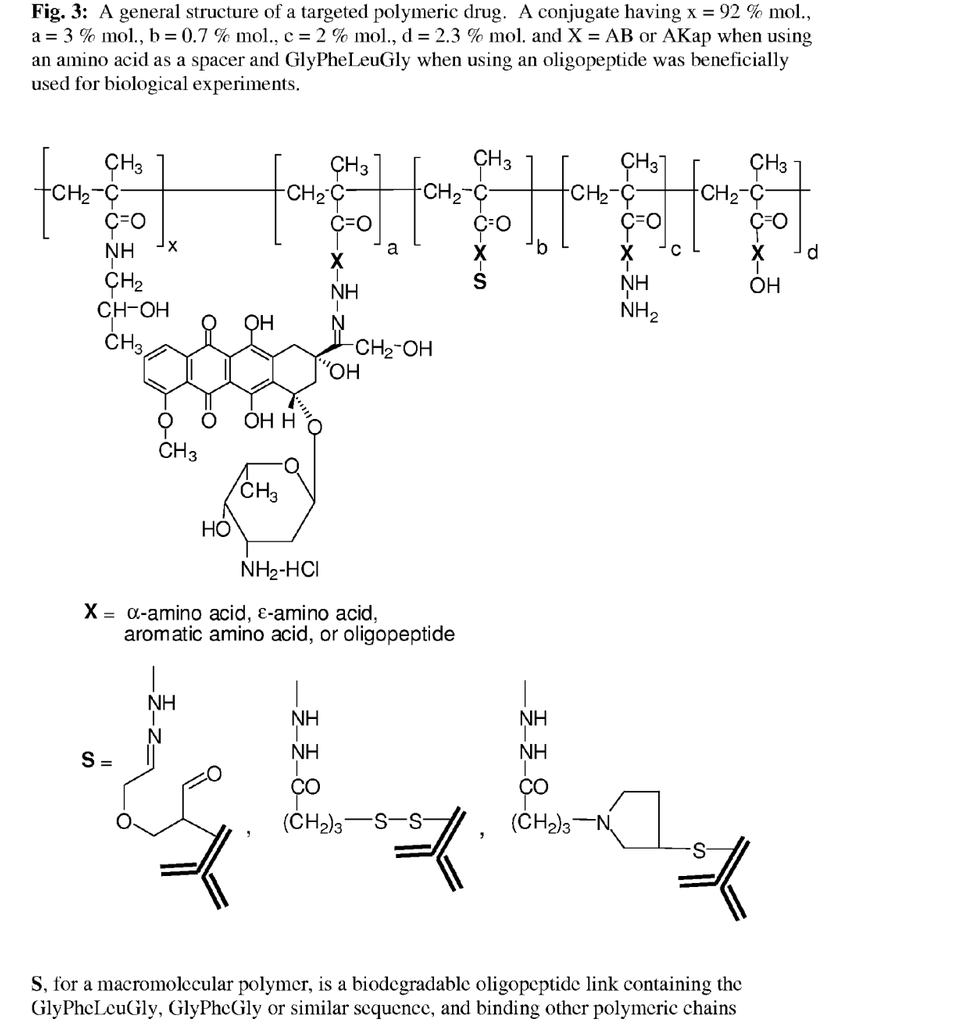
FIG. 3 shows the structure of a conjugate including the taregting antibody.

The invention provides linear and branched polymeric conjugates of doxorubicin, daunomycin, pharmorubicin and other anthracycline cancerostatic drugs containing a carbonyl group with copolymers prepared on the basis of N-(2-hydroxypropyl)-methacrylamide (HPMA) and optionally with antibodies, their fragments or non-specific immunoglobulin (FIG. 3). It is characteristic for these conjugates that the polymeric carrier along with the antibody (immunoglobulin) ensures prolonged circulation of the polymeric drug in blood vessels and its subsequent preferred passive or active accumulation in the tumor. The anti-cancer drug is attached to the carrier by a bond stable in the blood vessels (at pH 7.4). After the drug is linked to the polymer the cancerostatic loses its biological effect and is transported by the blood vessels in its inactive form. The cytotoxic drug only becomes activated intracellularly, in the organelles of the target cells, as pH decreases and the bond between the drug and the polymer is hydrolyzed.

The conjugates comprise a polymeric carrier formed by 30 to 3,000 monomer units linked to form a polymeric chain, 60 to 99% of them being constituted by N-(2-hydroxypropyl) methacrylamide units, 1 to 25% of them being the units of methacryloylated hydrazones of α-amino acids, ε-amino acids, aromatic amino acids or oligopeptides terminated by an anthracycline cancerostatic molecule (preferably doxorubicin) and 0.5 to 15% being the units of methacryloylated α-amino acids, ε-amino acids, aromatic amino acids or oligopeptides or their sodium salts; optionally, 0.5 to 10% units of methacryloylated hydrazides of α-amino acids, ε-amino acids, aromatic amino acids or oligopeptides are included and the conjugate may optionally include 0.5 to 5% of methacryloylated α-amino acids, ε-amino acids or oligopeptides terminated by a molecule of immunoglobulin or of a specific mono- or polyclonal antibody.

Apart from the above units, the branched macromolecular structures also contain 0.1 to 5% of units forming links that interconnect the individual polymeric chains to form the branched macromolecular structure, which links consist of enzyme-degradable methacryloylated oligopeptides, preferably tripeptides GlyPheGly, GlyLeuGly or tetrapeptide GlyPheLeuGly (SEQ ID NO:1), interconnected by diamines (ethylene diamine, hexamethylene diamine).

A characteristic of the polymeric conjugates with targeted anti-tumor action of this invention is the linkage between the active component—cytostatic—and the polymeric carrier via a hydrazone group formed in the reaction between the carbonyl group of the drug molecule and the polymer's hydrazide group. The linkage of the drug to the polymeric carrier significantly increases the drug's molecular weight resulting in prolonged time of circulation in the blood and of total retention time of the active component in the body. The linkage between the drug and the polymer is relatively stable during the drug transport in the blood vessels and hydrolytically cleavable in the slightly acidic environment inside the cells, namely in cellular organelles characterized by acidic pH. This means that the drug is transported through the blood vessels in its inactive form, linked to the polymer, and is only released and activated after its penetration to the target tumor cells. The drug activation in the target cells eliminates the side effects of the otherwise toxic cytostatics and focuses their effect preferentially on tumor cells. A polymeric carrier on the basis of HPMA copolymers is responsible for targeted transport to the tumor or tumor cells. When a branched high-molecular poly(HPMA) carrier is used the polymeric drug is stored in the solid tumor tissue due to passive targeting and the EPR effect Enhanced Permeability and Retention effect). The polymer may be released from the body following enzymatic degradation of the oligopeptide links in the form of shorter polymeric chains, for example by glomerular filtration. In carriers containing antibodies (immunoglobulin) the antibody is attached to the carrier via a hydrazone bond formed in reaction between the aldehyde groups, incorporated into an $F_C$ fragment of the antibody by sodium periodate oxidation, and the carrier's hydrazone groups. The antibody (immunoglobulin) may also be attached to the polymeric carrier chain using bifunctional agents. In such a case the antibody molecule is modified by reacting with 2-iminothiolane (introduction of —SH groups), maleimide groups are introduced into the polymer by reacting its hydrazide groups with succinimide ester of 3-maleimide propionic acid and the conjugation then occurs by addition of the —SH group of the antibody to the double bond of the polymer's maleimide group. Analogously, the conjugation may also be initiated by another bifunctional agent, such as SPDP (N-hydroxysuccinimide ester of 3-(2-pyridyldithio) propionic acid), which can be used to conjugate an —SH group containing antibody (immunoglobulin) directly to the hydrazide groups of the polymeric carrier.

The conjugate with the antibody (immunoglobulin) is accumulated in the target organs/tissues both passively and actively. Passive accumulation is enabled by the higher molecular weight of the conjugate and involves the so-called EPR effect, active accumulation is ensured by a process in which the binding site of the targeting antibody interacts with relevant receptors on the surface of the target cells. In the latter case the HPMA copolymer plays the role of both the carrier and a protective wrap significantly reducing immunogenicity of the targeting glycoprotein in the conjugate.

Figure 1:
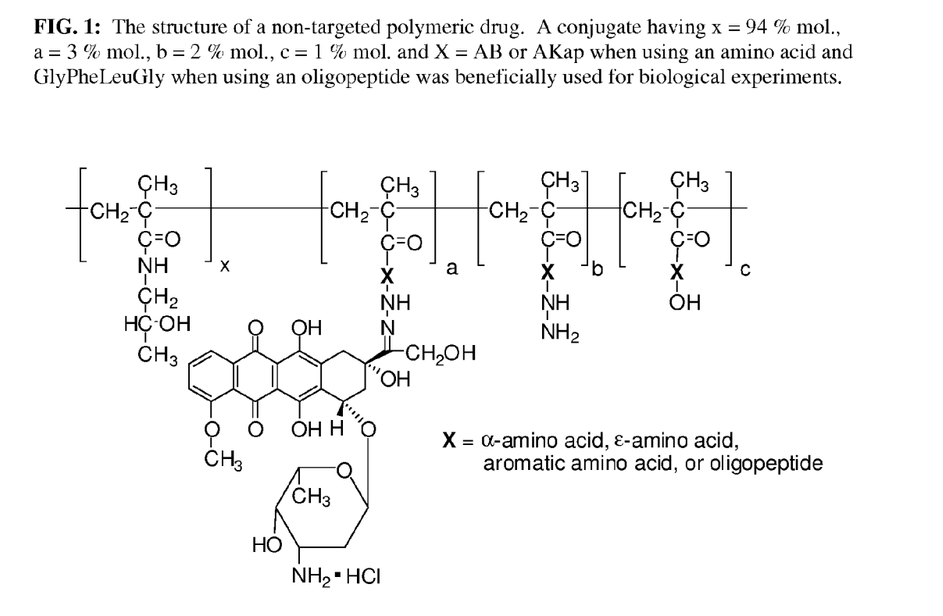
FIG. 1 shows the structure of a linear polymeric conjugate with a drug.
Figure 2:
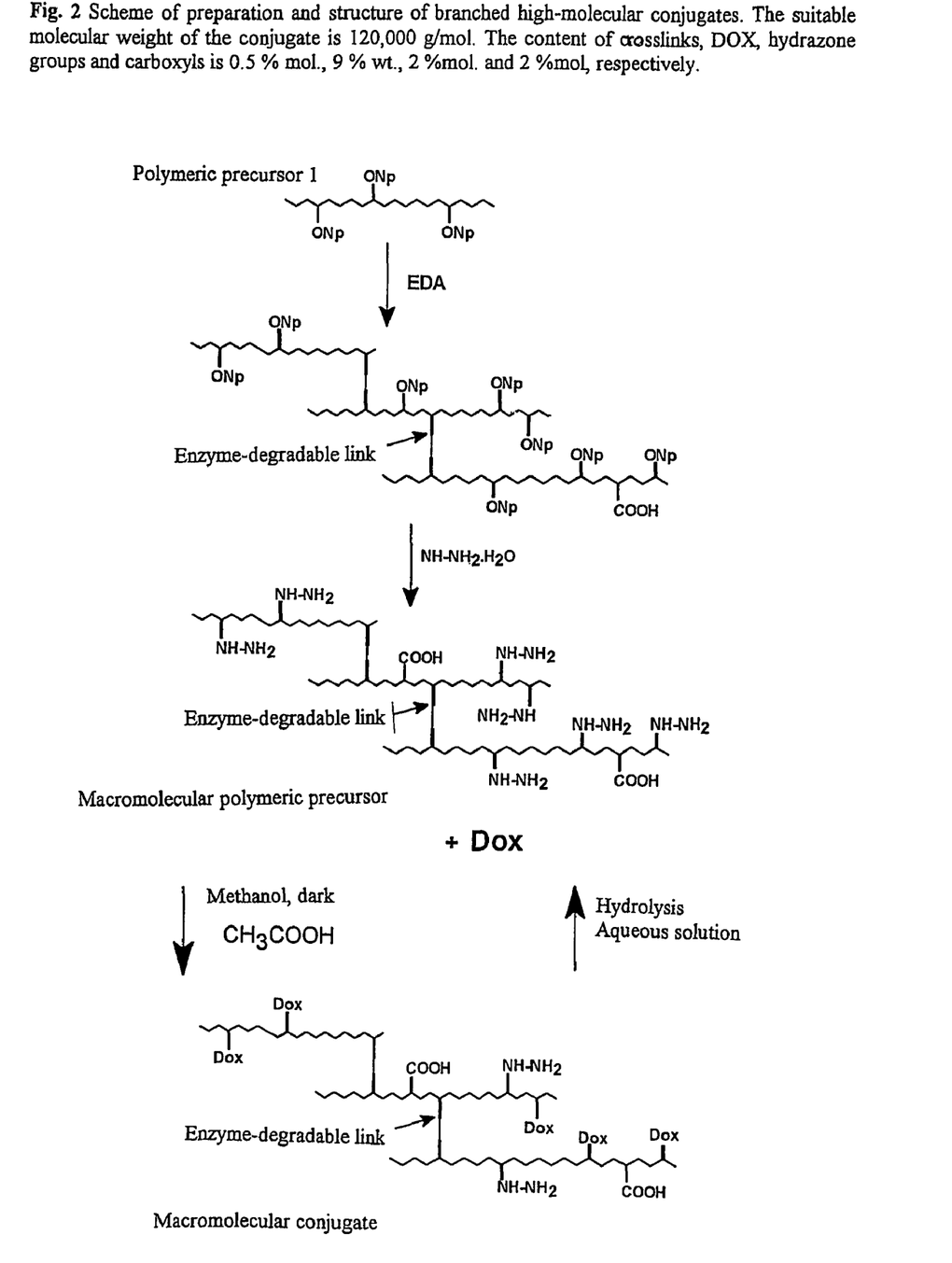
FIG. 2 shows a branched macromolecular structure of a polymer with biodegradable oligopeptide links.

The polymeric drug according to this invention can be used in three forms differing in their detailed structure. The first structure is represented by a linear polymeric conjugate with the drug without the targeting antibody (immunoglobulin) (FIG. 1); the second one is high molecular and represents a branched polymeric structure with biodegradable oligopeptide links (FIG. 2). The third structure includes also the targeting molecule (immunoglobulin) (FIG. 3).

Figure 4:
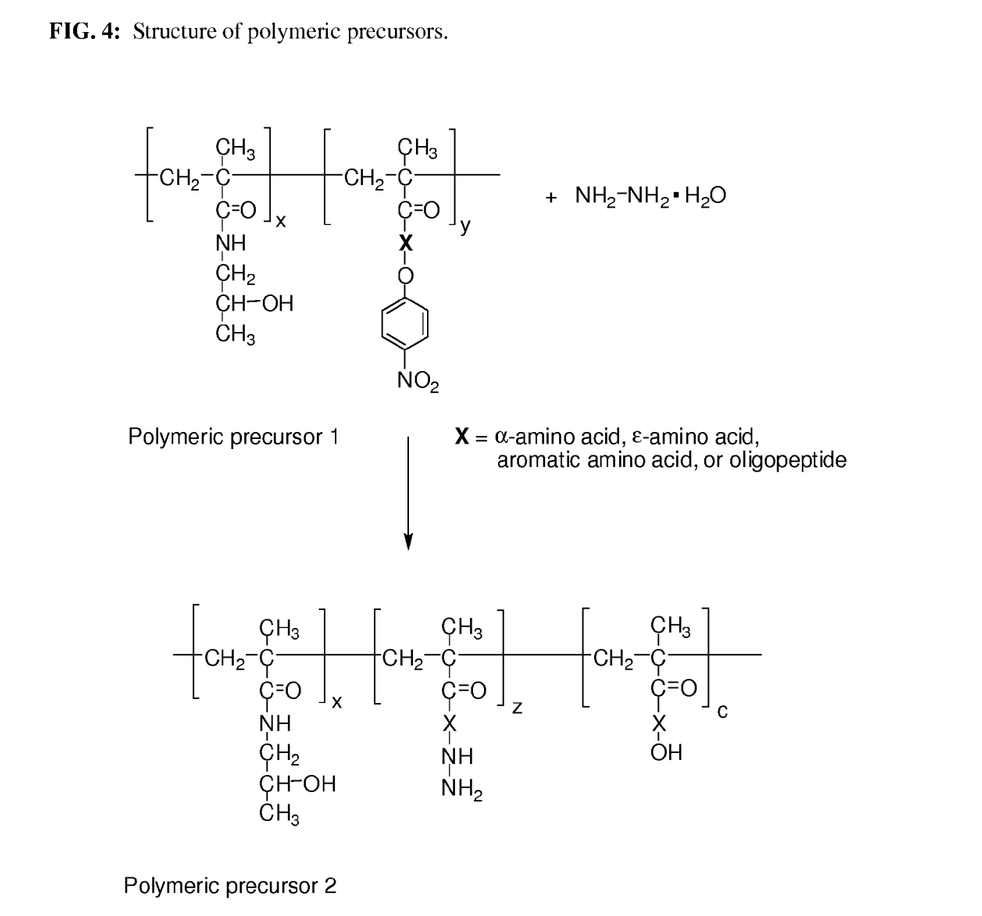
FIG. 4 shows a polymeric precursor.

Preparation of non-targeted linear polymeric drugs occurs in a plurality of reaction steps. The first step involves preparation of polymeric precursor I (see FIG. 4) as a copolymer of HPMA and methacryloylated reactive esters (4-nitrophenyl esters, N-hydroxysuccinimide esters, etc.) of amino acids or oligopeptides, the second step, leading to preparation of polymeric precursor II, involves hydrazinolytic transformation of the terminal ester groups to hydrazides. In the third step, a cancerostatic containing a keto group in the molecule is attached to the hydrazide groups by a chemical hydrazone bond.

Preparation of a branched polymeric drug needs to be started from polymeric precursor I containing an enzyme-degradable oligopeptide in its side chains, preferably GlyPheGly, GlyLeuGly, GlyPheLeuGly (SEQ ID NO:1) or GlyLeuPheGly (SEQ ID NO:2). The second step is initiated by slight branching of the polymer by reacting polymeric precursor I and alkylene diamine (ethyl, butyl, hexyl) and terminated by subsequent hydrazinolysis with hydrazine hydrate as described in the previous case.

Drugs targeted with antibodies (immunoglobulin) can be prepared from both previous types of drugs by subsequent reaction with an antibody (immunoglobulin) into the structure of which aldehyde groups have been previously introduced by mild oxidation with $KIO_4$ or $NaIO_4$ or by way of their conjugation with the antibody (immunoglobulin) using bifunctional agents as described above.

This invention can be used to prepare polymeric drugs for the treatment of various types of tumors in human medicine.

EXAMPLES

Example 1

Preparation of a Non-Targeted Linear Polymeric Drug Based on Doxorubicin

Synthesis of the polymeric drug was made in four synthetic steps. In the first step the monomers, N-(2-hydroxypropyl)methacrylamide (HPMA) and 4-nitrophenyl esters of a methacryloylated amino acid or oligopeptide (MA-X-ONp) were prepared. The second step was the preparation of polymeric precursor I by radical copolymerization of HPMA and MA-X-ONp. In the third step polymeric precursor II was prepared by hydrazinolysis of precursor I and in the last step linking of Dox to the polymeric precursor was effected.

Preparation of the Monomers:

HPMA was prepared by the method as described previously [Ulbrich 2000]. The methacryloylated reactive esters were prepared by methacryloylation of an appropriate amino acid or oligopeptide (X=Gly, diGly, GlyLeuGly, GlyPheGly, GlyPheLeuGly (SEQ ID NO:1), β-alanine, ε-amino caproic acid (AKap), p-amino benzoic acid (AB), etc.) by Schotten-Bauman reaction and by subsequent reaction of the resulting derivative of methacrylic acid with 4-nitrophenol in the presence of dicyclohexylcarbodiimide (DCCI).

Protocol for the Preparation of 4-Nitrophenyl Esters of Methacryloylated ε-Amino Acids The process of preparation of the MA-Gly-ONp, MA-GlyGly-ONp and MA-AB-ONp monomers is identical in all three cases. The preparative process for MA-AB-ONp is described below:

MA-AB-ONp: 0.024 mol (3.34 g) p-amino benzoic acid was dissolved in a triple-neck flask in 15 ml of a solution of 0.024 mol (0.97 g) sodium hydroxide. 0.024 mol (2.55 g) methacryloyl chloride and a solution of 0.024 mol (0.97 g) sodium hydroxide dissolved in 10 ml water were simultaneously added drop-wise to the aqueous solution of the sodium salt of the amino acid under stirring and cooling (5° C.). During the reaction the pH of the reaction mixture must not exceed pH 9. The reaction mixture was stirred for 1 hour and following its acidification to pH 2 the resulting white precipitate was filtered off on filter glass S4. The product was purified by crystallization from an ethanol-water mixture.

4-Nitrophenyl ester was prepared by reacting 0.014 mol (2.85 g) N-methacryloyl 4-amino benzoic acid with 0.014 mol (1.93 g) 4-nitrophenol in dimethylformamide at −10° C. in the presence of 0.0153 mol (3.16 g) dicyclohexylcarbodiimide. The reaction ran for 10 hours after which the precipitated dicyclohexylurea was filtered off and the product was purified by crystallization from an acetone-water mixture. The other two 4-nitrophenyl esters (MA-X-ONp) can be prepared in an analogous way.

The methacryloylated derivatives of GlyLeuGly, GlyPheGly, GlyPheLeuGly (SEQ ID NO:1), β-alanine and ε-amino caproic acid were also prepared by methacryloylation of oligopeptides or of an acid, however, following the acidification of the aqueous phase the methacryloylated acids had to be extracted into ethyl acetate and isolated by crystallization. The appropriate reactive esters (ONp esters) are prepared analogously as MA-AB-ONp except that the reaction medium for the esterification of MA-GlyLeuGly-OH and MA-GlyPheLeuGly-OH (SEQ ID NO:1) was tetrahydrofuran.

Preparation of polymeric precursor I: 1 g of a mixture of HPMA (95% mol, 0.89 g) and MA-AB-ONp (5% mol, 0.11 g) and 0.048 g azo-bis-isobutyronitrile were dissolved in 6.95 g acetone and the solution was placed in a polymerization ampoule. After the polymerization mixture was bubbled with nitrogen the ampoule was sealed up and the polymerization carried out at 50° C. for 24 hours. The pecipitated polymer was filtered off, rinsed for three times with acetone and diethyl ether and vacuum dried. The content of side chains terminated with reactive —ONp groups (the copolymer composition) can be controlled by the composition of the polymerization charge (the ratio of monomers). The same process was used to prepare all the polymeric precursors differing in the composition of the side chains.

Preparation of polymeric precursor II: The poly(HPMA-co-MA-AB-NHNH$_2$) copolymer was prepared by reacting polymeric precursor I with hydrazine hydrate. 300 mg polymeric precursor I ($1.3 \times 10^{-4}$ mol ONp) were dissolved in 2 ml methanol and a solution of 69 mg NH$_2$NH$_2$.H$_2$O in 1 ml methanol ($1.3 \times 10^{-3}$ mol. 10 fold excess relative to ONp) was added under intensive stirring. The reaction sure was left to react for 3 hours after which the methanol solution was diluted with distilled water to 30 ml and the product stripped of low-molecular components using dialysis against distilled water (2 days). The final product was isolated from the aqueous solution by lyophilization. The molecular weight ($M_w$) and polydispersity of the polymer were determined by means of gel chromatography equipped with a light dispersion detector. The amount of hydrazide groups was determined by spectroscopy following the reaction of hydrazide groups with TNBS (trinitrobenzenesulfonic acid). Precursors containing other amino acids and oligopeptides were prepared in the same manner. Polymeric precursors II were also prepared by radical precipitation copolymerization of the corresponding N-tert. butyloxycarbonylhydrazide of the methacryloylated oligopeptide or amino acid (poly(HPMA-co-MA-X-NHNH-BOC)) with HPMA under the conditions as described above. After the removal of the protective BOC group from poly(HPMA-co-MA-X-NHNH-BOC) with trifluoracetic acid polymeric precursors II were precipitated into an acetone-diethyl ether mixture, dissolved in water, dialyzed against water and lyophilized.

Linkage of doxorubicin to polymeric precursor: 250 mg of polymeric precursor II (poly(HPMA-co-MA-AB-NHNH$_2$) (0.1 mmol NHNH$_2$) were dissolved in 3 ml methanol. This polymer solution was added to 23 mg Dox.HCl (40 μmol). Two drops of acetic acid were added to the reaction mixture and the non-homogenous solution was stirred at laboratory temperature (in the dark). After reacting for 48 hours the homogenous solution was twice purified by gel filtration to separate free Dox in a column filled with Sephadex LH-20 in methanol. The polymeric fraction was isolated and concentrated in a vacuum evaporator. The product was re-precipitated from methanol into diethyl ether and dried until constant weight. The content of Dox and hydrazide groups was determined by spectroscopy ($\lambda$ 480 nm, $\epsilon$ 11 500 L mol$^{-1}$ cm$^{-1}$, water) and by TNBS, respectively. $<M_w>$ and molecular weight distribution were determined by liquid chromatography (Superose™6 (300×10 mm) column, 0.3 M acetate buffer (CH$_3$COONa/CH$_3$COOH; pH 6.5; 0.5 g/L NaN$_3$), flow rate 0.5 ml/min, detection by differential refractometer, light dispersion detector (DAWN-DSP-F, Wyatt Technology, USA) and UV detector (280 and 488 nm).

The above method was used to prepare all the other polymeric conjugates of doxorubicin.

Example 2

Preparation of a Branched Macromolecular Conjugate 400 mg of polymeric precursor I containing the oligopeptide sequences GlyPheGly, GlyLeuGly or GlyPheLeuGly (SEQ ID NO:1) (0.19 mmol ONp) were dissolved in 1.1 ml DMSO. 105 µl 0.2 M solution of 1,2-ethylene diamine in DMSO (21 µmol EDA) were added under vigorous stirring and the reaction mixture was left to react at laboratory temperature for 1 hour. A solution of 100 mg hydrazine hydrate (2 mmol) in 0.3 ml DMSO was added while intensely stiffing the polymer solution and the reaction mixture was vigorously stirred for another 3 hours. The reaction mixture was then diluted with distilled water to 30 ml and the product was purified by dialysis against distilled water (2 days). The high molecular precursor was lyophilized. $<M_W>$ and molecular weight distribution were determined by liquid chromatography, the content of hydrazide groups was determined spectroscopically by means of the TNBSA method. Doxorubicin was linked to the polymer and the conjugate was characterized under the same conditions as described in Example 1.

Example 3

Preparation of Antibody (Immunoglobulin)-Targeted Conjugate I

A copolymer bearing hydrazide and maleimide groups (MI) (poly(HPMA-co-MA-X-NHNH$_2$-co-MA-X-NHNH-MI)) in its side chains was prepared by partial modification of the hydrazide groups of polymeric precursor II containing 10 to 15% mol of hydrazide groups using N-hydroxysuccinimidyl ester of maleimidyl propionic acid (SMP). 250 mg of precursor II poly(HPMA-co-MA-diGly-NHNH$_2$) (125 µmol hydrazide groups) were dissolved in 1.2 ml DMSO and a solution of 16.6 mg SMP (62.5 µmol) in 0.6 ml DMSO was added. The reaction mixture was stirred at laboratory temperature for 8 hours. After purification in a PD-10 column (eluent: distilled water) $<M_w>$ and molecular weight distribution were determined by liquid chromatography, the amount of maleimide groups was determined by modified Ellman test and the content of residual hydrazide group was determined by the TNBS method. Doxorubicin was linked to this copolymer in the same manner as described in Example 1.

Introduction of —SH groups into the antibody (immunoglobulin) molecule: 15 mg of antibodies (polyclonal anti-thymocyte IgG) (0.1 µmol) were transferred into 1 ml phosphate buffer (0.05 M NaH$_2$PO$_4$/Na$_2$HPO$_4$; 0.1 M NaCl; 0.01 M EDTA; pH 7.4) in a PD-10 column. 0.67 mg 2-iminothiolan (4 µmol) were dissolved in 50 µl DMF and added to the solution of intensely stirred antibodies. After 2.5 hours of stirring at laboratory temperature the product was isolated by gel filtration in a PD-10 column (phosphate buffer, pH 7.4). The level of antibody (immunoglobulin) modification was determined by a method utilizing the reaction of —SH groups with the Ellman reagent.

Conjugation of 60 mg of poly(HPMA-co-MA-diGly-NHN=Dox-co-MA-X-NHNH$_2$-co-MA-X-NHNH-MI) containing doxorubicin, hydrazide and maleimide groups with 20 mg of modified antibodies was carried out in phosphate buffer of pH 7.4 (see above) at laboratory temperature. The final product was purified by gel filtration and characterized by means of UV spectroscopy (Dox content), amino acid analysis (antibody and immunoglobulin content) and electrophoresis with Phastsystem—Pharmacia LKB (presence of a free protein or drug).

Example 4

Preparation of Antibody (Immunoglobulin)-Targeted Conjugate II

In the first synthetic step polymeric precursor II was modified with SPDP under the similar conditions under which modification of the polymer with SMP was carried out in Example 3.

A solution of 42 mg of poly(HPMA-co-MA-diGly-NHN=Dox-co-MA-diGly-NHNH$_2$-co-MA-diGly-NHNH-PD) (containing 3.3 µmol of pyridyldithio (PD) groups) in 0.6 ml buffer was added to 14 mg of antibodies, immunoglobulin (see above) modified with —SH groups, containing 0.68 µmol of —SH groups dissolved in 1.7 ml phosphate buffer (0.05 M NaH$_2$PO$_4$/Na$_2$HPO$_4$; 0.1 M NaCl; 0.01 M EDTA, pH 7.4) while stirring. The reaction mixture was stirred at laboratory temperature for 7 hours after which the low-molecular portions and any unbound polymer were removed by gel filtration. The conjugate was then concentrated by ultrafiltration and characterized similarly as described in Example 3.

Example 5

Preparation of Antibody (Immunoglobulin)-Targeted Conjugate III

These conjugates were prepared by reacting antibodies into the molecules of which were aldehyde groups had been introduced by mild sodium periodate oxidation with hydrazide groups remaining after the reaction of polymeric precursor II with doxorubicin.

Preparation of oxidized antibodies: 40 mg of antibodies (polyclonal anti-thymocyte IgG) were transferred to acetate buffer (0.02 M CH$_3$COONa/CH$_3$COOH; 0.15 M NaCl; pH 5) using a PD-10 column. A 0.1 M solution of NaIO$_4$ was prepared in the same buffer in the dark. The solutions of antibodies and periodate were mixed in the ratio of 4:1 to reach the final concentrations of NaIO$_4$ and antibodies of 0.02 mol/l and 9 mg/l, respectively. The reaction mixture was stirred at laboratory temperature in the dark for 2 hours after which 25 µl ethylene glycol per each ml of the reaction mixture were added. After 20 minutes the oxidized antibodies (immunoglobulin) were purified and isolated by liquid chromatography in a PD-10 column. The concentration of antibodies (immunoglobulin) in the solution was determined by spectrophotometry. The number of aldehyde groups was determined by a method utilizing the reaction of aldehyde groups with the Lucifer Yellow CH dye.

Example of conjugate sample preparation: 36.5 mg of oxidized antibodies in 5 ml acetate buffer (0.02 M $CH_3COONa/CH_3COOH$; 0.15 M NaCl; pH 5) were, upon cooling to 15° C., mixed with a solution of 73 mg of poly(HPMA-co-MA-diGly-NHN=Dox-co-MA-diGly-$NHNH_2$) polymeric precursor II with bound Dox, dissolved in 1 ml buffer. The reaction mixture was stirred at 15° C. in the dark for 16 hours. After 16 hours the reaction mixture pH was adjusted to pH 7.2 with 0.1 M NaOH. The low-molecular portions and unbound polymer were removed from the conjugate by gel filtration. The conjugate was then concentrated and characterized in the same way as the other conjugates with antibodies (immunoglobulin).

Human and rabbit non-specific immunoglobulin (IgG), polyclonal anti-thymocyte antibodies (ATG), monoclonal antibodies anti-Thy 1.2, anti-CD4, anti-CD 71, anti-BCL1, anti-CD4, anti-CD8, anti-CD14 and other antibodies against tumor-associating antigens (anti-TAA) were used for conjugations with polymers.

Example 6

In Vitro Release of Doxorubicin from Polymeric Conjugates

Figure 5:
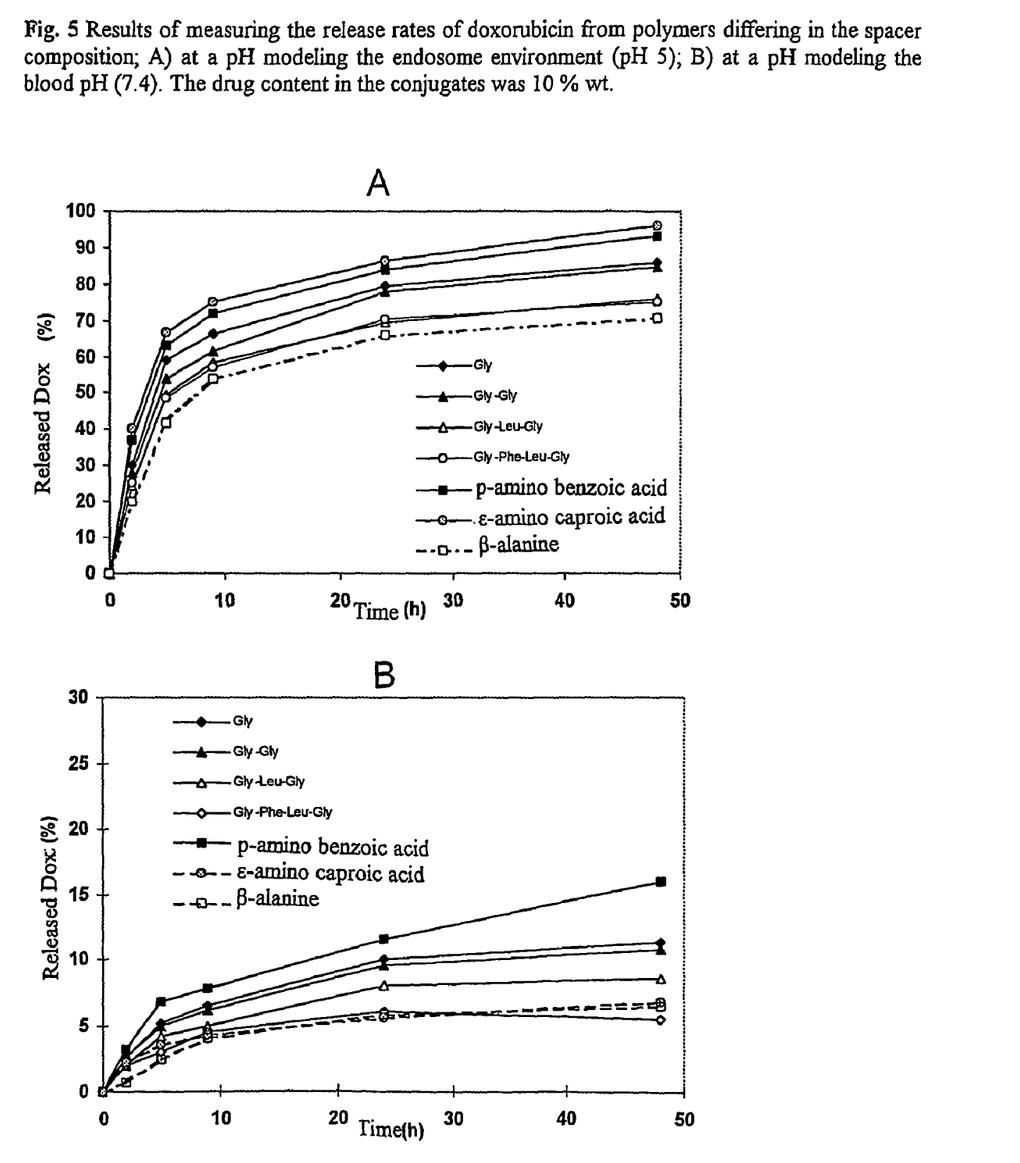
FIG. 5 shows the measurement results of the release rate of doxorubicin from the conjugates of this invention.

Hydrolytic stability of conjugates and the release rate of the active drug from the polymer were measured in model systems at various pH's and temperatures. FIG. 5 shows the measurement results of the release rates of doxorubicin from polymers differing in the spacer compositions at a pH modeling the blood pH (7.4) and at a pH modeling the endosome or lysosome environment (pH 5-6). The concentration of linked Dox (0.5 mmol·$l^{-1}$) was constant in 0.1 M acetate buffer ($CH_3COONa/CH_3COOH$, 0.05 M NaCl) in the experiments. The samples were incubated at 37° C. in the dark and 0.1 ml portions were taken in predefined intervals and analysed by means of HPLC after extraction of Dox from the solution. The results show that the structure of the link between the drug and the polymeric carrier influences the rate of release of the drug from the carrier the release rate being relatively low at the blood pH and more than ten times higher at a pH modeling the cellular environment. Considering the fact that the period of drug retention in the blood vessels is relatively short the experiment confirms the relative stability of the polymeric conjugate during transport and its ability to release the active drug first after its penetration in the cells.

Example 7

Figure 6:
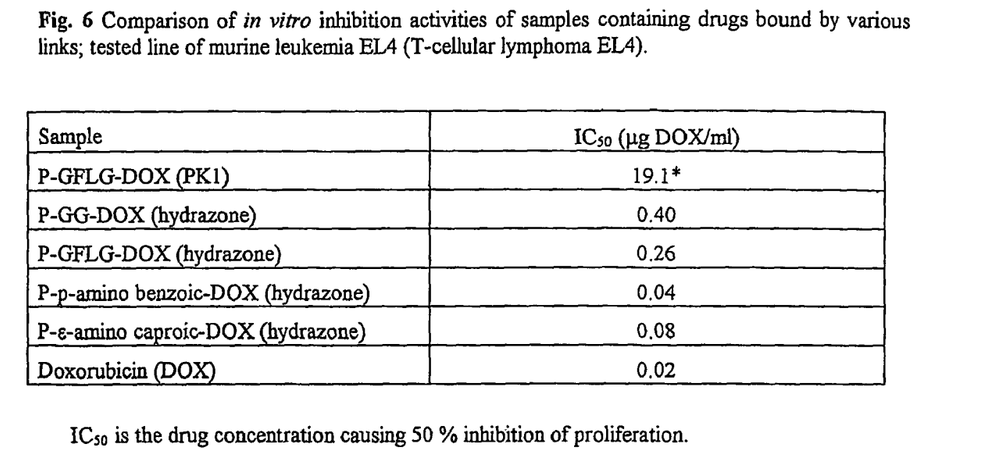
FIG. 6 shows the result of comparison of in vitro inhibition activities of the conjugates of this invention bound by means of various links.

In vitro Cytotoxic Activity of Polymeric Conjugates Containing Hydrolytically Released Doxorubicin in Cells with a Normal Lysosome Content (FIG. 6)

The ability of polymeric conjugates to reduce cell division or proliferation of target cells is called a cytotoxic or cytostatic activity. The cytotoxic activity was detected in vitro by inhibition of incorporation of $^3H$-thymidine to the target cell nuclei [Říhová et al, 2000]. Incorporation of thymidine and the activity of conjugates are indirectly proportional. Low incorporation of thymidine means high cytotoxic activity of tested substances. The cells of selected tumor lines (mouse T leukemic line EL4, mouse B cellular leukemia BCL1, mouse B cellular lymphoma 38C13, primary human colorectal carcinoma SW 480, metastasizing human colorectal carcinoma SW 620, human colorectal carcinoma SW620 genetically modified by mouse gene for Thy 1.2 SW620/T) and mouse splenocytes stimulated by T-cellular mitogen, i.e. concanavalin A, and human peripheral lymphocytes were pipetted in the amounts of $1 \times 10^4$-$5 \times 10^5$ (depending on the testing cell systems used) in growth medium RPMI 1640 into 96-well FB-tissue plates (NUNC, Denmark). Subsequent cultivation was carried out either without further stimulation (all tumor lines and unaffected murine and human lymphocytes) or in the presence of the T-cellular mitogen of concanavalin A, when the effect on normal, intensively proliferating T-lymphocytes was to be studied. The concentration of concanavalin A in which the cells were cultivated was 1.25 µg/well. Test samples or free doxorubicin in final concentrations of 0.0016-80 µg/ml were added to each experimental well of the tissue plate containing test cells in a medium with or without concanavalin A. The total well volume was 250 µl. Each concentration was tested on a parallel basis in one sample and one line three to five times. The microtitration tissue plates were incubated at 37° C. in the atmosphere of 5% $CO_2$ for 24 to 72 hours. After completing the cultivation 1 µCi of $^3H$-thymidine was added to each well. After another five or six hours (depending on the testing system) the cells were collected (Tomtec cell collector) on a glass fiber filter (Filtermat, Wallac), dried and evaluated for radioactivity incorporated (MicroBeta Trilux, Wallac). $IC_{50}$ for non-targeted conjugates containing hydrolytically released doxorubicin ranged from 0.01 µg doxorubicin/ml to 1.41 µg doxorubicin/ml depending on the resistance (sensitivity to treatment of the target line used) and on the type of conjugate. It was confirmed that cytotoxicity is an exclusive property of conjugates containing hydrolytically released doxorubicin since a conjugate without the drug is not cytotoxic.

The in vitro tests have proved that a) the activity of conjugates with a hydrolytically releasable drug does not depend on enzymatic degradability of the covalent bond between the drug and the oligopeptide link and that b) the conjugates where the link between the basic polymeric chain and the drug is only formed by e-amino caproic acid or p-amino benzoic acid are equally effective as those containing a di- or tetrapeptide link.

Example 8

Figure 7:
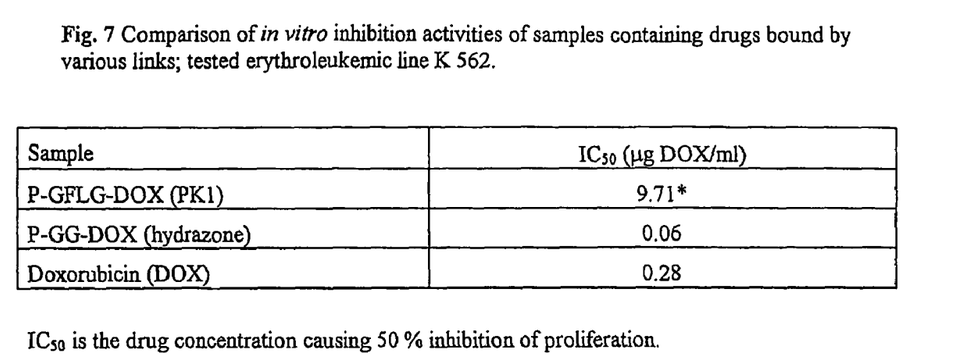
FIG. 7 shows the result of comparison of in vivo inhibition activities of the conjugates of this invention bound by means of various links.

In Vitro Cytotoxic Activity of Polymeric Conjugates Containing Hydrolytically Released Doxorubicin in Cells with Low Lysosome Content An in vitro test of cytotoxic activity was carried out in the same manner as described in Example 7. Cells of erythroleukemic line K 562 with low lysosome content were selected as the target cells. It has been proved that the conjugates containing hydrolytically released doxorubicin are significantly cytotoxic even in this line in which the conjugates with enzymatically released doxorubicin are cytotoxic to a very limited extent (FIG. 7). This result shows that conjugates with hydrolytically released doxorubicin are effective even in cell systems poor in lysosomes.

Example 9

Figure 8:
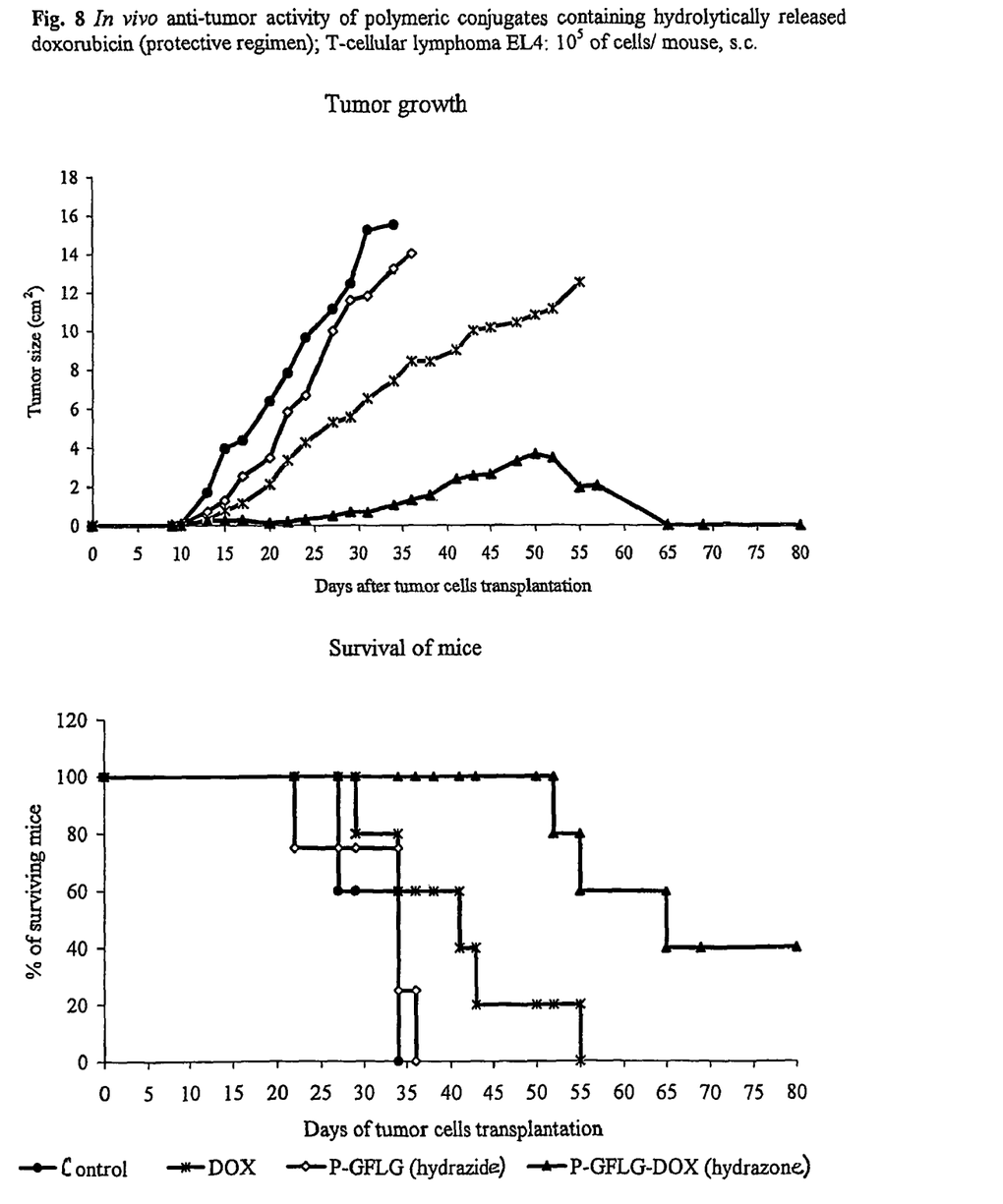
FIG. 8 shows the results of in vivo studies of anti-tumor activities of the conjugates of this invention.

In vivo Anti-Tumor Activity of Polymeric Conjugates Containing Hydrolytically Released Doxorubicin (FIG. 8)

Mice of inbred strain C57BL/10 were subcutaneously transplanted with T-cellular lymphoma (EL4). The tumor cells were injected in the lower half of the back of experimental animals in the amount of 1×10⁵ cells/mouse. The cell transplantation day was marked day 0. Polymeric conjugates with hydrolytically released doxorubicin were then administered intraperitoneally either on day 1, 3, 5, 7 and 9 (protective regimen), on day 10, 12, 14, 16 and 18 or on day 12, 14, 16, 18 and 20 (therapeutic regimen). The daily dose of doxorubicin was 50 μg/mouse. The conjugates significantly inhibited tumor growth and increased the number of long-term surviving experimental animals. While a drug-free polymeric conjugate had no effect at all and the classic, i.e. non-modified, doxorubicin had a very limited effect (maximum survival period of the experimental animals was 40 days as opposed to 35 days in the control group), administration of polymeric conjugates with hydrolytically released doxorubicin enabled long-term survival, i.e. more than 80 days, in 40% and 20% of mice in the protective regimen and therapeutic regimen, respectively.

Mice of inbred strain Balb/c were i.p. transplanted with mouse B-cellular leukemia BCL1. The tumor cells were injected in the amount of 5×10⁵ cells/mouse. The cell transplantation day was marked day 0. Polymeric conjugates with hydrolytically released doxorubicin were then administered intravenously on day 11, 13 and 17 (therapeutic regimen). The daily dose of doxorubicin was 100 μg/mouse. The tested conjugates had significant anti-tumor activity. While the control mice survived no longer than 40 days, 20% of mice treated with the tested conjugates survived longer than 100 days and 10% longer than 140 days.

REFERENCES

R. Duncan, J. B. Lloyd, J. Kopeček, P. Rejmanová, J. Strohalm, K. Ulbrich, B. Říhová, V. Chytrý: Synthetic Polymeric Drugs. Czech. PV 0095/85, Australia 589587, Canada 130053, Denmark 164485, Europe 0187547, U.S. Pat. No. 5,037,883, Japan 000137786

K. Ulbrich, V. Šubr, J. Strohalm, D. Plocová, M. Jelínková, B. Říhová, Polymeric Drugs Based on Conjugates of Synthetic and Natural Macromolecules I. Synthesis and Physico-chemical Characterisation. *J. Controlled Rel.* 64, 63-79 (2000)

Vasey P. A., Kaye S. B., Morrison R., Twelves C., Wilson P., Duncan R., Thomson A. H., Murray L. S., Hilditch T. E., Murray T., Burtles S., Fraier D., Frigerio E. Cassidy, J.: Phase I clinical and pharmacokinetic study of PK1 [N-(2-hydroxypropyl)methacrylamide copolymer doxorubidin]: first member of a new class of chemotherapeutic agents—drug polymer conjugates, Clinical Cancer Research 5, 83-94 (1999)

Julyan, P. J., Seymour, L. W., Ferry, D. R., Daryani, S., Boivin, C H. M., Doran, J., David, M., Anderson, D., Christodoulou, C H., Young, A. M., Hesslewood, S., Kerr, D. J.: Preliminary clinical study of the distribution of HPMA copolymers bearing doxorubicin and galactosamine, J. Control. Rel. 57, 281-290 (1999)

Thomson A. H., Vasey P. A., Murray L. S., Cassidy J., Fraier D., Frigerio E., Twleves C.: Population pharmacokinetics in phase I drug development: a phase I study of PK1 in patients with solid tumors, Br. J. Cancer. 81, 99-107 (1999)

J. Kopeček P. Kopečková, T. Minko, Z. Lu, HPMA Copolymer-Anticancer Drug Conjugates: Design, Activity, and Mechanism of Action. Europ. J. Pharm. Biopharm. 50, 61-81 (2000)

F. Kratz, U. Beyer, H. T. Schutte, Drug-Polymer Conjugates Containing Acid-Cleavable Bonds. Critical Reviews "in Therapeutic Drug Carriers Systems", 16(3), 245-288 (1999)

B. Říhová, T. Etrych, M. Pechar, M. Jelínková, M. Šťastný, O. Hovorka, M. Kovář, K. Ulbrich, Doxorubicin Bound to a HPMA Copolymer Carrier Through Hydrazone Bond is Effective also in a Cancer Cell Line with a Limited Content of Lysosomes. *J. Controlled Release* 74, 225-232 (2001)

Tomáš Etrych, Markéta Jelínková, Blanka Říhová, Karel Ulbrich, New HPMA copolymers containing doxorubicin bound via pH sensitive linkage. Synthesis, in vitro and in vivo biological properties. *J. Controlled Rel.* 73, 89-102 (2001)

The invention claimed is:

1. A conjugate comprising monomeric units linked to form a polymeric chain, wherein
   (a) 60 to 99% of the monomeric units are N-(2-hydroxypropyl)methacrylamide;
   (b) 1 to 25% of the monomeric units are methacryloylated hydrazones formed from an aliphatic keto group of an anthracycline cancerostatic and a methacryloylated hydrazide, wherein each methacryloylated hydrazide is independently selected from the group consisting of: C-hydrazides of N-methacryloyl-α-amino acids, C-hydrazides of N-methacryloyl-ε-amino acids, C-hydrazides of N-methacryloyl aromatic amino acids, and C-hydrazides of oligopeptides methacryloylated on their terminal amino group; and
   (c) 0.5 to 15% of the monomeric units are independently N-methacryloyl-α-amino acids, N-methacryloyl-ε-amino acids, N-methacryloyl aromatic amino acids, or oligopeptides methacryloylated on their terminal amino group; or sodium salts of any of these.

2. The conjugate of claim 1, further comprising 0.5 to 5% of monomeric units of N-methacryloyl-α-amino acids, N-methacryloyl-ε-amino acids or N-methacryloyl-oligopeptides methacryloylated on their terminal amino group, each of said monomeric units being independently terminated by an immunoglobulin molecule.

3. The conjugate of claim 1, further comprising 0.1 to 5% of monomeric units of enzyme-degradable N-methacryloyl oligopeptides methacryloylated on their terminal amino group, through which monomeric units on two polymer chains of the conjugate are interlinked by an alkylene diamine.

4. The conjugate of claim 1, wherein the anthracycline cancerostatic is doxorubicin.

5. The conjugate of claim 1, further comprising: (d) 0.5 to 10% of the monomeric units are methacryloylated hydrazides, wherein each methacryloylated hydrazide is independently selected from the group consisting of: C-hydrazides of N-methacryloyl-α-amino acids; C-hydrazides of N-methacryloyl-ε-amino acids, C-hydrazides of N-methacryloyl aromatic amino acids, and C-hydrazides of oligopeptides methacryloylated on their terminal amino group.

6. The conjugate of claim 2 of the general formula wherein is a schematic depiction of an immunoglobulin, and wherein the individual monomeric units are disposed in a random manner in the polymeric chain and where X is a suitable link formed by each amino acid or oligopeptide residue, x ranges from 20 to 3,000, a ranges from 1 to 750, b ranges from 1 to 450, c ranges from 1 to 450, and d ranges from 1 to 150.

7. The conjugate of claim 1 wherein each amino acid or oligopeptide is independently selected from the group consisting of: Gly, Ala, Leu, GlyGly, GlyLeuGly, GlyPheGly, GlyPheLeuGly (SEQ ID NO:1), β-alanine, ε-amino caproic acid, and p-amino benzoic acid.

8. The conjugate of claim 2 wherein the immunoglobulin molecule is selected from the group consisting of: γ-globulin, an autologous antibody, and an antibody which binds a tumor-associated antigen.

9. The conjugate of claim 3 wherein the units linking the polymeric chains are chosen from the group consisting of: GlyPheLeuGly (SEQ ID NO:1), GlyLeuGly, GlyPheGly, GlyLeuPheGly (SEQ ID NO:2).

10. A pharmaceutical composition comprising a conjugate of claim 1.

11. A pharmaceutical composition comprising a conjugate of claim 2.

12. The conjugate of claim 5 of the general formula wherein the individual monomeric units are disposed in a random manner in the polymeric chain and where X is a suitable link formed by each amino acid or oligopeptide residue, x ranges from 20 to 3,000, a ranges from 1 to 750, b ranges from 1 to 450 and c ranges from 1 to 450.

13. The conjugate of claim 1, wherein the conjugate contains 30 to 3,000 monomeric units linked to form the polymeric chain.

14. The conjugate of claim 2, wherein the immunoglobulin molecule is a monoclonal antibody or a polyclonal antibody.

15. The conjugate of claim 8, wherein the immunoglobulin molecule is an antibody that binds a tumor-associated antigen.

16. The conjugate of claim 15, wherein the antibody is anti-17-1A or anti-CA 15-3.

17. The pharmaceutical composition of claim 11, wherein the immunoglobulin molecule is an antibody which binds a tumor-associated antigen.

18. The conjugate of claim 5, wherein the anthracycline cancerostatic is doxorubicin.

19. The conjugate of claim 5, wherein the conjugate contains 30 to 3,000 monomeric units linked to form the polymeric chain.

20. A pharmaceutical composition, comprising a conjugate of claim 5.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: synthetically constructed polymeric chain

<400> SEQUENCE: 1

Gly Phe Leu Gly
 1

<210> SEQ ID NO 2
<211> LENGTH: 4
<212> TYPE: PRT
<213> ORGANISM: Artificial Sequence
<220> FEATURE:
<223> OTHER INFORMATION: synthetically constructed polymeric chain

<400> SEQUENCE: 2

Gly Leu Phe Gly
 1